Oct. 7, 1969 D. L. ARMSTRONG Plant Pat. 2,928
ROSE PLANT
Filed Jan. 17, 1968
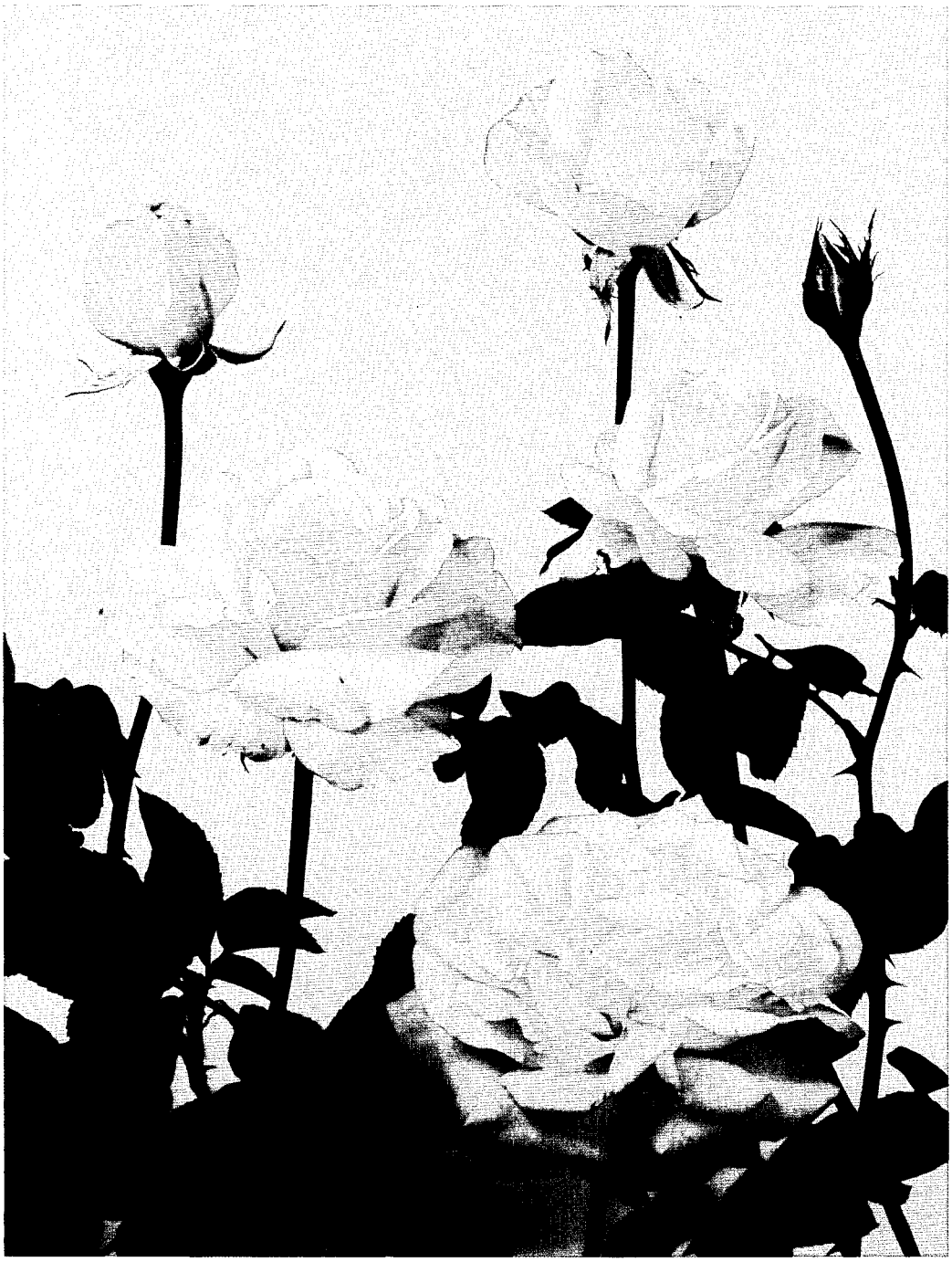
Inventor.
D. L. Armstrong
By: Robb & Robb
Attorneys.

United States Patent Office

Plant Pat. 2,928
Patented Oct. 7, 1969

2,928
ROSE PLANT

David L. Armstrong, Ontario, Calif., assignor to Armstrong Nurseries, Inc., Ontario, Calif., a corporation of California

Filed Jan. 17, 1968, Ser. No. 698,672
Int. Cl. A01h *5/02*
U.S. Cl. Plt.—19 1 Claim

The present invention relates to a new and distinct variety of rose plant of the hybrid tea class, which was originated by me by crossing the rose variety known as "Queen Elizabeth" (Plant Patent No. 1,259) with the rose variety known as "Chrysler Imperial" (Plant Patent No. 1,167), the former being the seed parent and the latter being the pollen parent.

The new variety resulted from an extensive breeding program conducted by me and having for its objective the production of new and improved rose varieties in the grandiflora and hybrid tea classes which bear flowers in the pink and red color range, and particularly combining therewith the vigor and attractive plant habit of the parent variety "Queen Elizabeth" and the better flower qualities and greater flower petalage of the parent variety "Chrysler Imperial." This objective was fully achieved, along with other desirable features, as evidenced by the following unique combination of characteristics which are outstanding in the new variety and which distinguish it from its parents, as well as from all other rose varieties of which I am aware:

(1) A very vigorous and upright-spreading plant habit;

(2) Attractive, medium to large, semiglossy foliage which covers the plant well;

(3) A habit of bearing the flowers usually singly on medium to long stems of good strength;

(4) Double flowers of medium size, with a good urn-shaped bud form and a high-centered open flower form; and (5) A distinctive and attractive dark pink or light red flower color ranging between Carmine and Rose Madder, and usually being somewhat darker in color on the reverse side of the petals.

In comparision with its seed parent "Queen Elizabeth," the new variety bears the flowers more singly; the flowers are larger and more double; and the flower color is a considerably darker pink color.

As compared with its pollen parent "Chrysler Imperial," the new variety has a more vigorous plant habit, and the flowers range from pink to light red color instead of being of red color like the flowers of this parent.

Asexual reproduction of my new variety by budding, as performed at Ontario, Calif., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Robert F. Wilson's Horticultural Colour Chart (hereinafter abbreviated (W)) and Robert Ridgway's Color Standards and Nomenclature (hereinafter abbreviated (R)), as indicated:

Type: Tall; bush; outdoor; seedling; for cut flowers and for garden decoration.

Class: Hybrid tea.

Breeding: Seedling.

*Seed parent.*—"Queen Elizabeth."

*Pollen parent.*—"Chrysler Imperial."

Propagation: Holds its distinguishing characteristics through succeeding propagations by budding.

FLOWER

Locality where grown and observed: Ontario, Calif.

Flowers borne: Usually singly, but sometimes two or three or more to stem; in irregular clusters; on normal to strong stems of medium to long length.

Quantity of bloom: Free, outdoors.

Continuity: Nearly continuous during growing season.

Fragrance: From slight to moderate.

Bud:

*Peduncle.*—From average length to long; from average caliper to heavy; erect; usually smooth; with none to few very small stipitate glands. Color—near Buffy Brown, Plate XL (R), overlaid with near Indian Red Plate XXVII (R) on side exposed to sun.

*Before calyx breaks.*—Size—from small to medium. Form—short; ovoid.

*As calyx breaks.*—Color—between Ruby Red, Plate 827, page 171 (W) and Pansy Purple, Plate 928/1, page 177 (W).

*Sepals.*—Usually with foliaceous appendages extending from ¼ to ⅔ sepal length. Inner surface—with fine, wooly tomentum. Outer surface—usually smooth. Alternate margins—lined with fine, wooly tomentum. Other margins—with few to several small stipitate glands and small, slender foliaceous parts.

*As first petal opens.*—Size—small. Form—from short to medium length; from ovoid to urn-shaped. Color: outside—between Crimson, Plate 22/1, page 22 (W) and Rose Madder, Plate 23/1, page 23 (W); inside—between Carmine, Plate 21/1, page 21 (W) and Crimson, Plate 22/2, page 22 (W), with small area at base of petals near Dresden Yellow, Plate 64/3, page 64 (W).

*Opening.*—Opens up well; is not retarded or prevented from opening by cold, hot, wet or dry weather.

Bloom:

*Size (when fully open).*—Average; from 3¾ inches to 4½ inches.

*Petalage.*—Double; from 30 to 35 petals, plus 6 to 10 petaloids; arranged irregularly.

*Form.*—High-centered at first, but becoming cupped to high-centered; petals being at first somewhat tightly cupped, with tips reflexed outward, but later becoming more loosely cupped at maturity, with tips reflexed outward; intermediate and outside petals of both newly opened and three days open flower usually reflexed outward along apex and sometimes also along edges of petal.

Petals:

*Texture.*—Medium thickness; moderately leathery.

*Appearance.*—Inside—satiny. Outside—satiny.

*Shape.*—Outside—broadly obovate, with apex flat and usually with 2 or 3 notches. Intermediate—between round and obovate, with apex rounded and sometimes with 1 or 2 notches. Inside—between round and obovate, with apex rounded and sometimes with 1 or 2 notches.

This description of a newly opened flower was made from a rose grown outdoors during the month of November at Ontario, Calif.:

*Color.*—Outer petal: outside surface—between Crimson, Plate 22/1, page 22 (W) and Rose Madder, Plate 23/1, page 23 (W); inside surface—between Carmine, Plate 21/1, page 21 (W) and Rose Madder, Plate 23/2, page 23 (W), with small area at base of petal near Dresden Yellow, Plate 64/3, page 64 (W). Intermediate petal: outside surface—between Crimson, Plate 22/1, page 22 (W) and Rose Madder, Plate 23/1, page 23 (W); inside surface—between Carmine, Plate 21/1, page 21 (W) and Crimson, Plate 22/2, page 22 (W), with small area at base of petal near Primrose Yellow, Plate 601/3, page 65 (W). Inner petal: outside surface—between Carmine, Plate 21/1, page 21 (W) and Rose Madder, Plate 23/1, page 23 (W); inside surface—between Carmine, Plate 21/1, page 21 (W) and Crimson, Plate 22/1, page 22 (W), with small area at base of petal near Dresden Yellow, Plate 64/3, page 64 (W).

This description was made from a rose that was open for three days outdoors during the month of October at Ontario, Calif.:

*Color.*—Outer petal: outside surface—between Rose Madder, Plate 23/1, page 23 (W) and Tyrian Rose, Plate 24/2, page 24 (W); inside surface—between Crimson, Plate 22/2, page 22 (W) and Rose Madder, Plate 23/2, page 23 (W). Inner petal: outside surface—between Rose Madder, Plate 23/2, page 23 (W) and Tyrian Rose, Plate 24/2, page (W); inside surface—between Rose Madder, Plate 23/2, page 23 (W) and Tyrian Rose, Plate 24/3, page 24 (W).

*General color effect.*—Newly opened flower—between Carmine, Plate 21/1, page 21 (W) and Rose Madder, Plate 23/2, page 23 (W). Three days open—between Crimson, Plate 22/2, page 22 (W) and Tyrian Rose, Plate 24/3, page 24 (W).

*Behavior.*—Drop off cleanly; not particularly affected by cold, hot, wet or dry weather.

*Flower longevity.*—On bush in garden—3 or 4 days in November. Cut roses grown outdoors and kept at living-room temperatures—2 or 3 days in November.

REPRODUCTIVE ORGANS

Stamens: Average number; arranged regularly about pistils; a few mixed with petaloids.

Filaments: From short to medium length (from 5 mm. to 10 mm. long); most with anthers. Color—near French Rose, Plate 520/1, page 136 (W).

Anthers: From small to medium size; all open approximately at once. Color: upper side—margins near Cadmium Orange, Plate 8/2, page 8 (W), with remainder near Empire Yellow, Plate 603/2, page 66 (W); under side—margins near Cadmium Orange, Plate 8/2, page 8 (W), with remainder near Empire Yellow, Plate 603/2, page 66 (W).

Pollen: From sparse to moderate abundance. Color—near Tangerine Orange, Plate 9/1, page 9 (W).

Pistils: From average number to many (approximately 130 in number).

Styles: Uneven; short; thin; bunched. Color—upper ¼ of style near Crimson, Plate 22, page 22 (W), with remainder near Empire Yellow, Plate 603/2, page 66 (W).

Stigma: Color—near Apricot, Plate 609/2, page 70 (W).

Ovaries: Usually all enclosed in calyx.

Hips: From short to average length; globular; smooth; walls thick and fleshy. Color (½ mature)—near Lime Green, Plate XXXI (R).

Sepals: Falling soon; medium length. Color: inside—near Light Drab, Plate XLVI (R); outside—near Rainette Green, Plate XXXI (R).

Seeds: From small to medium size; from 5 to 10 in number.

PLANTS

Foliage:

*Leaves.*—Compound of usually 3 to 7 leaflets; abundant; from medium size to large; leathery; semi-glossy.

*Leaflets.*—Shape—broadly oval. Apex—acute. Base—round. Margin—simply serrate.

*Color.*—Mature: upper surface—near Forest Green, Plate XVII (R); under surface—near Chromium Green, Plate XXXII (R). Young: upper surface—near Cress Green, Plate XXXI (R); under surface—near Mignonette Green, Plate XXXI (R).

*Rachis (the supporting stem of the compound leaf).*—From average size to heavy. Upper side—grooved; with several to many stipitate glands on edges. Under side—smooth; with none to few stipitate glands and none to few small prickles.

*Stipules.*—From short to medium length; medium width; with short points turning out at an angle of more than 45°.

*Disease resistance.*—Better than average resistance to mildew, as determined by comparsion with other varieties grown under comparable conditions at Ontario, Calif.

Growth:

*Habit.*—Upright-spreading; much-branched.

*Growth.*—Very vigorous.

*Canes.*—Heavy.

*Main stems.*—Color—near Mignonette Green, Plate XXXI (R). Large prickles—several; from medium length to long; hooked slightly downward; with medium length, narrow base; color—near Russet, Plate XV (R). Small prickles—few; color—near Russet, Plate XV (R). Hairs—none.

*Branches.*—Color—near Absinthe Green, Plate XXXI (R). Large prickles—several; from medium length to long; hooked slightly downward; with medium length, narrow base; color—near Sayal Brown, Plate XXIX (R). Small prickles—few; color—near Sayal Brown, Plate XXIX (R). Hairs—none.

*New shoots.*—Color—near Absinthe Green, Plate XXXI (R), overlaid with near Dark Vinaceous-Brown, Plate XXXIX (R) on side exposed to the sun. Large prickles—from few to several; medium length; hooked slightly downward; with short to medium length, narrow base; color—near Mineral Red, Plate XXVII (R). Small prickles—few; color—near Mineral Red, Plate XXVII (R). Hairs—none.

I claim:

1. A new and distinct variety of rose plant of the hybrid tea class, substantially as herein shown and described, characterized particularly as to novelty by the unique combination of a very vigorous and upright-spreading plant habit, attractive, medium to large, semi-glossy foilage which covers the plant well, a habit of bearing the flowers usually singly on medium to long stems of good strength, double flowers of medium size, with a good urn-shaped bud form and a high-centered open flower form and a distinctive and attractive dark pink or light red flower color ranging between Carmine and Rose Madder, and usually being somewhat darker in color on the reverse side of the petals.

No references cited.

ROBERT E. BAGWILL, Primary Examiner